United States Patent
Inoue

(12) 
(10) Patent No.: US 6,274,306 B1
(45) Date of Patent: Aug. 14, 2001

(54) CARRIER FOR EXTRACTING BACTERIA, METHOD OF EXTRACTING MICROORGANISM AND METHOD OF ASSAYING MICROORGANISMS

(75) Inventor: Takakazu Inoue, Ushiku (JP)

(73) Assignees: Sanyo Electric Co., Ltd., Osaka-fu; Society for Techno-Innovation of Agriculture, Forestry and Fisheries, Tokyo, both of (JP)

( * ) Notice: Subject to any disclaimer, the term of this patent is extended or adjusted under 35 U.S.C. 154(b) by 0 days.

(21) Appl. No.: 09/282,749

(22) Filed: Mar. 31, 1999

(30) Foreign Application Priority Data

Mar. 17, 1999 (JP) .................................................. 11-071485

(51) Int. Cl.[7] .............................. C12Q 1/00; C12Q 1/68; C12P 19/34; C07H 21/04
(52) U.S. Cl. ..................... 435/4; 435/6; 435/7; 435/91.1; 435/91.2; 435/283; 536/23.1; 536/24.31; 536/24.32
(58) Field of Search .................................. 435/6, 7, 91.1, 435/91.2, 261, 174, 260, 262, 262.5, 283, 4; 536/23.1, 24.31, 24.37, 24.33

(56) References Cited

U.S. PATENT DOCUMENTS 4,104,127 * 8/1978 Bucalo .................................. 195/127
5,658,795 * 8/1997 Kato et al. ......................... 435/262.5
5,863,789 * 1/1999 Komatsu et al. ..................... 435/262

FOREIGN PATENT DOCUMENTS

| 5-192147 | 8/1993 | (JP) . |
| 7-255482 | 10/1995 | (JP) . |
| 09290284 | * 11/1997 | (JP) . |
| 10156387 | * 6/1998 | (JP) . |

OTHER PUBLICATIONS

JP09290284 Nakamura et al abstract Nov. 1997.*

JP10156387 Mastubayashi abstract Jun. 1998.*

* cited by examiner

Primary Examiner—Kenneth R. Horlick
Assistant Examiner—Jeffrey Siew
(74) Attorney, Agent, or Firm—Akin, Gump, Strauss, Hauer & Feld,L.L.P.

(57) ABSTRACT

A carrier for extracting bacteria is formed by a material body having a plurality of pores with no DNA. The pores are 5 to 100 $\mu$m in mean pore diameter, and at least 5 $\mu$m in depth. Bacteria enter the pores of the carrier for extracting bacteria buried in a sampling site and inhabit therein. After a lapse of a prescribed time, the carrier for extracting bacteria is taken out and washed for removing large-sized foreign matter. Further, the carrier for extracting bacteria is crushed to liberate the bacteria.

17 Claims, 5 Drawing Sheets

F I G. 6
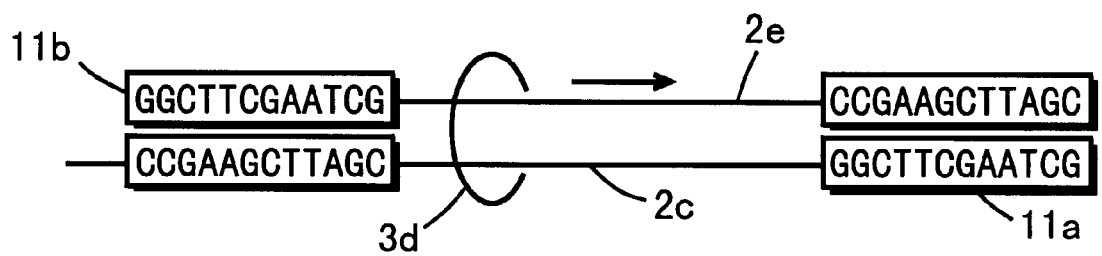
F I G. 7
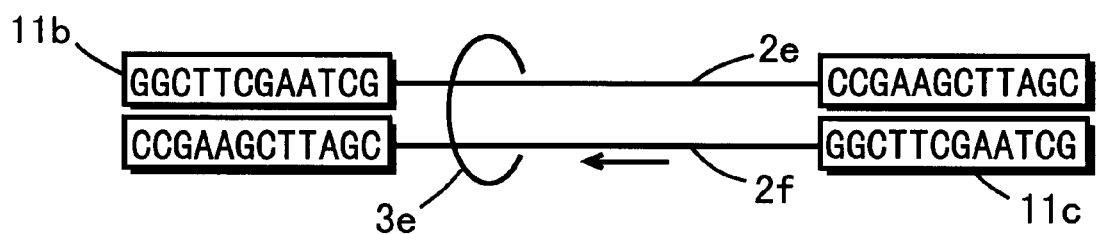

CARRIER FOR EXTRACTING BACTERIA, METHOD OF EXTRACTING MICROORGANISM AND METHOD OF ASSAYING MICROORGANISMS

BACKGROUND OF THE INVENTION

1. Field of the Invention

The present invention relates to a carrier for extracting bacteria, a method of extracting a microorganism and a method of assaying microorganisms.

2. Description of the Prior Art

In recent years, a garbage disposal for composting organic waste (the so-called kitchen garbage) discharged from a household kitchen or the like is now actively researched and developed. In the garbage disposal, microorganisms such as bacteria and protozoa degrade organic matter to form compost. During the composting process (organic degradation process) in such a garbage disposal, the degree of composting is evaluated by monitoring the temperature or the like. The state of the garbage disposal is adjusted to prepare high-quality compost on the basis of the evaluation.

In order to prepare high-quality compost, it is necessary to obtain information of the microorganisms (at least the types of the microorganisms) functioning in the garbage disposal. The information of the microorganisms is also necessary for excellently controlling degradation of the kitchen garbage with the microorganisms. In order to improve soil by adding the prepared compost, it is also important to obtain information of microorganisms contained in the soil.

In general, information of microorganisms is obtained by a method of sampling soil, wood chips or food containing bacteria, extracting the bacteria therefrom, isolating each bacterium included in the extracted bacteria and biochemically examining the same.

In order to examine bacteria in a garbage disposal, wood chips contained in the tank of the garbage disposal to serve as a treating carrier are sampled. The wood chips are introduced into a large quantity of sterilized physiological salt solution for liberating the bacteria from the wood chips by a suspension method. This solution is filtered through a filter for removing foreign matter such as the wood chips, large-sized protozoa and the like. The filtrate is further centrifuged for extracting the bacteria in the supernatant.

After extracting the bacteria in the aforementioned manner, the centrifuged supernatant is further diluted and inoculated on an agar medium. The bacteria are cultured in the agar medium, and each bacterium included in the bacteria is isolated. Each bacterium thus isolated is biochemically examined, for obtaining information of the microorganisms.

The wood chips employed as a treating carrier in the garbage disposal are composed of plant cell, and so they may have DNA. When analyzing DNA of the bacteria in the tank, therefore, the wood chips must be completely separated from the bacteria. Therefore, the treatment step by the suspension method and the filtration step with the filter are required as described above, to complicate the steps of extracting the bacteria.

Further, time is required for isolating each bacterium from the bacteria formed by a plurality of bacteria, and it is difficult to analyze bacteria which are hard to isolate by this method.

On the other hand, a PCR (polymerase chain reaction) method is employed for amplifying DNA. In the PCR method, a primer having a base sequence complementary to that at both ends of DNA (template DNA) to be amplified and heat-resistant DNA polymerase are employed for repeating a cycle formed by three stages of a thermal denaturation step, an annealing (heat treatment) step and an extension reaction step thereby enabling amplification of DNA fragments substantially identical to the template DNA. Employing this PCR method, a prescribed fragment in DNA of one of a small amount of bacteria can be amplified to hundred thousand to million times, for example.

In order to employ the PCR method, however, the base sequence of at least at both ends of a part of the template DNA must be known. If the types and base sequences of microorganisms functioning in the garbage disposal or existing in soil are unknown, therefore, DNA fragments of the microorganisms cannot be amplified in the conventional PCR method.

In this regard, there has been proposed a RAPD (random amplified polymorphic DNA) method or AP-PCR (arbitrarily primed-polymerase chain reaction) method of simultaneously amplifying a large amount of DNA fragments from a single type of DNA with a single primer, with no information of the base sequence. According to this method, the annealing temperature for the primer is reduced while the magnesium ion concentration in a reaction solution is increased during the PCR, thereby reducing sequence specificity of the primer in bonding. Thus, the primer is bonded to chromosome DNA of a microorganism with mismatching, to duplicate DNA fragments.

According to the RAPD method or AP-PCR method, some DNA fragments are amplified in a large amount with a single primer, with no information on the base sequence of the DNA to be amplified. A DNA fingerprint is obtained by separating the amplified DNA fragments by gel electrophoresis. The state of the microorganism can be analyzed by analyzing the DNA fingerprint.

When applying a conventional PCR method such as the RAPD (random amplified polymorphic DNA) method or the AP-PCR (arbitrarily primed-polymerase chain reaction) method to bacteria formed by a plurality of bacteria in analysis of chromosome DNA prepared from the bacteria, chromosome DNA of the bacteria can be readily associated with amplified DNA fragments and the efficiency of the analysis is improved by adjusting the primer and PCR conditions for setting the probability of amplification at a low value so that a single DNA fragment is amplified for $10^8$ bp (base pairs), for example. When discriminating a group of bacteria formed by a plurality of bacteria, however, the number of types of amplified DNA fragments is so large that it is difficult to associate a bacterium which is a template with amplified DNA fragments, and hence it is difficult to discriminate an ecosystem formed by the group of bacteria.

SUMMARY OF THE INVENTION

An object of the present invention is to provide a carrier for extracting bacteria which can simplify extraction of bacteria.

Another object of the present invention is to provide a method of extracting a microorganism which can readily extract a microorganism.

Still another object of the present invention is to provide a method of assaying microorganisms which can correctly discriminate a plurality of microorganisms.

A carrier for extracting bacteria according to an aspect of the present invention comprises a material body having a plurality of pores with no DNA, while the mean pore diameter of the pores is at least 5 μm and not more than 100 μm and the depth of each pore is at least 5 μm.

The carrier for extracting bacteria is arranged on a site for sampling bacteria for a prescribed time and thereafter recovered. After the recovered carrier for extracting bacteria is washed, the bacteria are liberated from the carrier for extracting bacteria.

The aforementioned carrier for extracting bacteria has a plurality pores suitable for inhabitation of bacteria, so that bacteria enter the pores and inhabit therein in a concentrated state. When recovering the carrier for extracting bacteria, therefore, the bacteria can be sampled from the sampling site in a concentrated state.

The bacteria, which enter the pores and inhabit therein, are hardly removed when washing the carrier for extracting bacteria. On the other hand, foreign matter etc. larger than the pores not entering the pores is readily removed by washing. Thus, a filtration step for separating the bacteria from the foreign matter can be shortened.

When liberating the bacteria from the carrier for extracting bacteria by crushing the carrier for extracting bacteria, DNA of the bacteria can be analyzed with no hindrance even if the extracted bacteria contain the carrier for extracting bacteria since the carrier for extracting bacteria is formed by the material body having no DNA. Therefore, the carrier for extracting bacteria may not be completely separated from the bacteria, and so the number of steps required for extracting microorganisms can be reduced.

Thus, bacteria can be readily extracted by employing the inventive carrier for extracting bacteria.

The material body may be made of plastic, synthetic fiber, ceramic, metal, glass or paper. A carrier for extracting bacteria formed by such a material body has no DNA.

The material body may contain a nutrient preferred by a microorganism. Thus, bacteria gather and inhabit in the carrier for extracting a microorganism, whereby the bacteria can be sampled in a further concentrated state.

The material body may be made of a material degradable by a microorganism.

In this case, bacteria capable of degrading the material body forming the carrier for extracting bacteria gather and inhabit in the carrier for extracting bacteria. Thus, bacteria capable of degrading the material body can be sampled in a concentrated state. Further, the carrier for extracting bacteria itself is degraded by the bacteria, whereby the speed of degradation by the bacteria and the degradation state can be examined by measuring the weight, the degree of polymerization etc. of the carrier for extracting bacteria.

A method of extracting a microorganism according to another aspect of the present invention comprises steps of arranging a carrier for extracting a microorganism formed by a material body having a plurality of pores with no DNA on a site for sampling microorganisms, recovering the carrier for extracting a microorganism after a lapse of a prescribed time, and liberating the microorganisms from the recovered carrier for extracting a microorganism.

In the method of extracting a microorganism, the carrier for extracting a microorganism having a plurality of pores is arranged on the site for sampling microorganisms, whereby a microorganism can be sampled in a concentrated state. The microorganism, which enters any pore of the carrier for extracting a microorganism and inhabits therein, is hardly removed from the carrier for extracting a microorganism also when the carrier is washed. Therefore, only foreign matter etc. larger than the pores can be removed. Thus, the microorganism can be readily extracted.

The pores of the carrier for extracting a microorganism preferably have a mean pore diameter and a depth suitable for the size of the microorganism included in the microorganisms to be extracted. Thus, microorganisms gather and inhabit in the pores of the carrier for extracting a microorganism, whereby the microorganisms to be extracted can be sampled in a concentrated state.

The method of extracting a microorganism may further comprise a step of liberating the microorganisms by crushing the carrier for extracting a microorganism.

In this case, DNA of the microorganism can be analyzed with no hindrance even if the microorganism contains the crushed carrier for extracting a microorganism since the carrier for extracting a microorganism is formed by the material body having no DNA. Therefore, a step for completely removing the carrier for extracting a microorganism from the microorganism is deleted for simplifying extraction of the microorganism.

The method of extracting a microorganism may further comprise steps of detaching the microorganisms from the carrier for extracting a microorganism by ultrasonic treatment. Thus, the carrier for extracting a microorganism can be separated from the microorganisms.

The method of extracting a microorganism may further comprise steps of crushing the carrier for extracting a microorganism and detaching the microorganisms from the crushed carrier by ultrasonic treatment and sedimenting or centrifuging the crushed carrier and the microorganisms. Thus, the carrier for extracting a microorganism can be separated from the microorganisms.

The method of extracting a microorganism may further comprise steps of crushing the carrier for extracting a microorganism by ultrasonic treatment and centrifuging the crushed carrier and the microorganisms. Thus, the carrier for extracting a microorganism can be separated from the microorganisms.

The method of extracting a microorganism may further comprise a step of impregnating the carrier for extracting a microorganism with a nutrient preferred by a microorganism. Thus, microorganisms gather and inhabit in the carrier for extracting a microorganism, whereby the microorganisms can be sampled in a further concentrated state.

The material body may be that degradable by a microorganism.

In this case, bacteria capable of degrading the material body forming the carrier for extracting a microorganism gather and inhabit in the carrier for extracting a microorganism. Thus, a microorganism capable of degrading the material body can be sampled in a concentrated state. Further, the carrier for extracting a microorganism itself is degraded by this microorganism, whereby the speed of degradation by the microorganism and the degradation state can be examined by measuring the weight and the degree of polymerization of the carrier for extracting a microorganism.

The material body may be made of hardly degradable plastic. Alternatively, the material body may be made of biodegradable plastic.

A method of assaying microorganisms according to still another aspect of the present invention comprises steps of extracting a group of microorganisms with a carrier for extracting a microorganism having a plurality of pores with no DNA, crushing the carrier for extracting a microorganism with the extracted group of microorganisms, preparing a plurality of primers having different amplification probabilities, simultaneously applying a polymerase chain reaction method of repeating a thermal denaturation step, a primer annealing step and an extension reaction step with polymerase in this order to DNA of a plurality of different microorganisms included in the extracted group of microorganisms with each of the plurality of primers thereby amplifying DNA fragments of the DNA of the plurality of different microorganisms included in the microorganisms, classifying the amplified DNA fragments by a discrimination method, and discriminating the plurality of different microorganisms included in the group of microorganisms.

In the method of assaying microorganisms, the carrier for extracting a microorganism having a plurality of pores is arranged on a site for sampling microorganisms for a prescribed period and thereafter recovered for sampling microorganisms in a concentrated state. The carrier for extracting a microorganism is crushed thereby liberating the microorganisms from the carrier for extracting a microorganism. In this case, the carrier for extracting a microorganism is formed by a material body having no DNA, whereby DNA of the microorganisms can be analyzed with no hindrance even if the microorganisms contain the carrier for extracting a microorganism.

The polymerase chain reaction method is simultaneously applied to DNA of a plurality of different microorganisms extracted in the aforementioned manner with each of the plurality of primers having different amplification probabilities, whereby DNA fragments can be amplified from the plurality of different microorganisms. Thus, the plurality of microorganisms included in the extracted group of microorganisms can be correctly discriminated.

By employing the plurality of primers having different amplification probabilities, further, a plurality of types of DNA fragments are obtained from a microorganism. Thus, a plurality of information can be obtained from each microorganism included in the group of microorganisms, for improving the precision of assay. Consequently, various microorganic ecosystems can be correctly assayed in a short time.

While the number of types of microorganisms forming the group of microorganisms to be assayed and the size of chromosome DNA of the microorganisms are generally unknown, results of amplification by primers for amplifying a proper number of types of DNA fragments can be selected from an electrophoretic pattern by simultaneously employing primers having different amplification probabilities or different orders of amplification probabilities.

By employing a plurality of primers having a proper amplification probability selected in the aforementioned manner, DNA fragments can be amplified from microorganisms also when the number of types of microorganisms forming the group of microorganisms are unknown, for examining the number of types of the microorganisms forming the group of microorganisms from the number of types of the amplified DNA fragments.

By employing the plurality of primers having a proper amplification probability selected in the aforementioned manner, DNA fragments can be amplified from a principal microorganism or principal group of microorganisms also when the type of the principal microorganism forming the group of microorganisms is unknown, for predicting the size of chromosome DNA of the principal microorganism or the principal group of microorganisms from the number of types of the amplified DNA fragments. Further, it is possible to examine whether microorganisms forming the principal group of microorganisms belong to bacteria, actinomycetes or protozoa from the predicted size of the chromosome DNA.

The amplifying step may include steps of preparing an apparatus for amplifying DNA fragments having a plurality of reaction solution storage parts and arranging the plurality of primers having different amplification probabilities in the plurality of reaction solution storage parts respectively.

In such an apparatus for amplifying DNA fragments, the plurality of primers having different amplification probabilities are arranged in the plurality of reaction solution storage parts respectively, whereby DNA fragments of DNA of a plurality of microorganisms having different base values can be simultaneously amplified by simultaneously applying the polymerase chain reaction method to the DNA of the plurality of different microorganisms with each of the plurality of primers having different amplification probabilities. Thus, a plurality of microorganisms included in the group of microorganisms can be correctly discriminated.

The discrimination method may be electrophoresis. In this case, the amplified DNA fragments are classified by the electrophoresis. Thus, the amplified DNA fragments appear as bands classified in response to the size in an electrophoretic pattern. The number of types of the plurality of different microorganisms can be examined by analyzing the patterns of the bands.

The method of assaying microorganisms may further comprise steps of applying a polymerase chain reaction method of repeating a thermal denaturation step, a primer annealing step and an extension reaction step with polymerase in this order to DNA of a microorganism related to a contaminant with each of the plurality of primers having different amplification probabilities thereby amplifying a DNA fragment of the DNA of the microorganism, classifying the DNA fragment amplified from the microorganism by the discrimination method, preserving the relation between the type of the microorganism and the result of classification in a database, and retrieving the types of the plurality of different microorganisms from the database on the basis of the results of classification of the DNA fragments amplified from the plurality of different microorganisms.

In this case, the DNA fragment of the DNA of the microorganism related to the contaminant is amplified by the polymerase chain reaction method employing each of the plurality of primers having different amplification probabilities and this DNA fragment is classified by the discrimination method. The result of classification of the DNA fragment thus obtained and the type of the microorganism related to the contaminant are preserved in the database. On the other hand, DNA fragments of DNA of a plurality of microorganisms included in the group of microorganisms extracted by the carrier for extracting a microorganism with a plurality of primers similar to the above are amplified by the polymerase chain reaction method and these DNA fragments are classified by a classification method similar to the above. The plurality of microorganisms included in the group of microorganisms can be correctly discriminated by analyzing the results of classification of the DNA fragments of the DNA of the plurality of different microorganisms thus obtained. Further, a microorganism related to the contaminant included in the extracted group of microorganisms can be specified by retrieving the type of the microorganism from the database on the basis of the results of classification. Thus, a contaminant contained in the site for sampling the microorganisms can be predicted.

The method of assaying microorganisms may further comprise a step of determining presence/absence of the contaminant in the site for sampling the microorganisms on the basis of the result of retrieval of the database. The method of assaying microorganisms may further comprise a step of determining the degree of the quantity of the contaminant.

Thus, the contaminant contained in the site for sampling the microorganisms and the contamination state can be effectively predicted, whereby the contaminant in the sampling site can be assayed by an analytical method suitable for the predicted contaminant.

The database preferably preserves a plurality of types of microorganisms and results of classification corresponding thereto.

Thus, a plurality of types of microorganisms related to the contaminant can be specified. Thus, a plurality of types of contaminants contained in the sampling site can be simultaneously assayed.

The discrimination method may be electrophoresis, the results of classification may be band patterns of an electrophoretic pattern, and the database may preserve the relation between the type of the microorganism and the band patterns of the electrophoretic pattern.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 6 is a model diagram showing the process in a first time of a second cycle in the random PCR method (GGCTTCGAATCG is SEQU ID NO: 1 and CCGAAGCTTAGC and SEQ ID NO: 2); and FIG. 7 is a model diagram showing the process in a second time of the second cycle in the random PCR method (GGCTTCGAATCG is SEQ ID NO: 1 and CCGAACGTTAGC is SEQ ID NO: 2).

DESCRIPTION OF THE PREFERRED EMBODIMENTS

Figure 1:
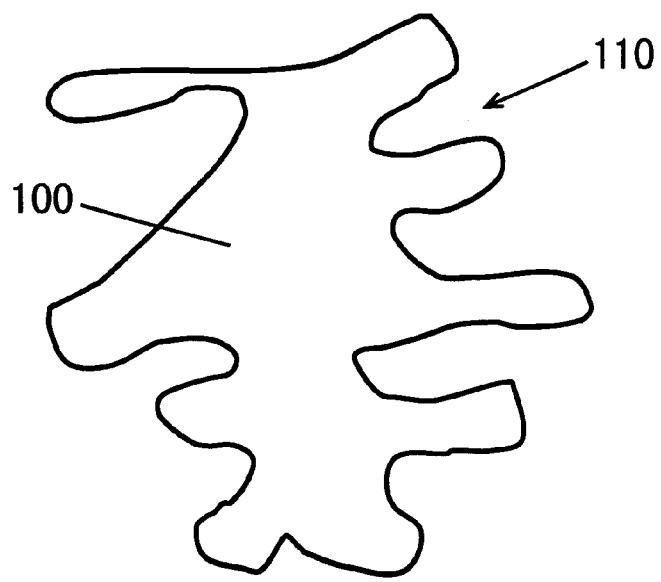
FIG. 1 is a model sectional view showing a carrier for extracting bacteria according an embodiment of the present invention.

FIG. 1 is a model sectional view showing carrier for extracting bacteria according to an embodiment of the present invention.

A bacteria extractive carrier 100 shown in FIG. 1 is made of a material having no DNA. This bacteria extractive carrier 100 has a plurality of pores 110 with a surface having an irregular shape. Thus, the bacteria extractive carrier 100 has a large surface area.

The material for and the shape of the bacteria extractive carrier 100 preferably readily allow separation of bacteria by ultrasonic treatment, or can preferably be readily crushed and separated from microorganisms by centrifugation.

The material for the bacteria extractive carrier 100 is prepared from organic matter such as plastic, synthetic fiber, ceramic, metal, glass or paper, for example.

The pores 110 of the bacteria extractive carrier 100 are preferably 5 to 100 μm in mean pore diameter and at least 5 μm in depth. When extracting a specific bacterium, the pore diameter is preferably suitable for inhabitation of the extracted bacterium. Thus, the bacterium is habitable in any pore 110 while foreign matter larger than the pore diameter can be prevented from entering the pores 110.

The pore diameter distribution of the bacteria extractive carrier 100 can be measured by mercury penetration employing a mercury porosimeter.

The bacteria extractive carrier 100 may be impregnated with a single nutrient or a plurality of combined nutrients preferred by bacteria such as various amino acids, peptone, a meat extract, a yeast extract, a malt extract, vitamins, saccharides, alcohols, nitrate, ammonium salt, sulfate, thiosulfate, phosphate, potassium, sodium, magnesium, calcium, iron, copper, manganese, cobalt and zinc, for example. Further, the bacteria extractive carrier 100 can preferably keep constant water retention as well as a higher temperature than the peripheral environment. Thus, the bacteria extractive carrier 100 attains environment suitable for inhabitation of bacteria, to readily gather bacteria.

A method of extracting bacteria employing the bacteria extractive carrier 100 shown in FIG. 1 is now described.

In the following description, bacteria are extracted from the tank of a garbage disposal with the bacteria extractive carrier 100 shown in FIG. 1.

Wood chips are contained into the tank of the garbage disposal as a treating carrier, and the bacteria extractive carrier 100 shown in FIG. 1 is embedded in the wood chips. In this case, the tank contains only a small amount of bacteria.

Then, a constant quantity of kitchen garbage is introduced into the tank while the contents of the tank are stirred. This operation is repeated for a prescribed period. During the prescribed period, the temperature and humidity in the tank are kept in states excellent for the treatment.

Following the aforementioned introduction of the kitchen garbage, the types and the number of the bacteria contained in the tank are increased. The bacteria inhabit in the wood chips contained in the tank as well as in the bacteria extractive carrier 100.

Figure 2:
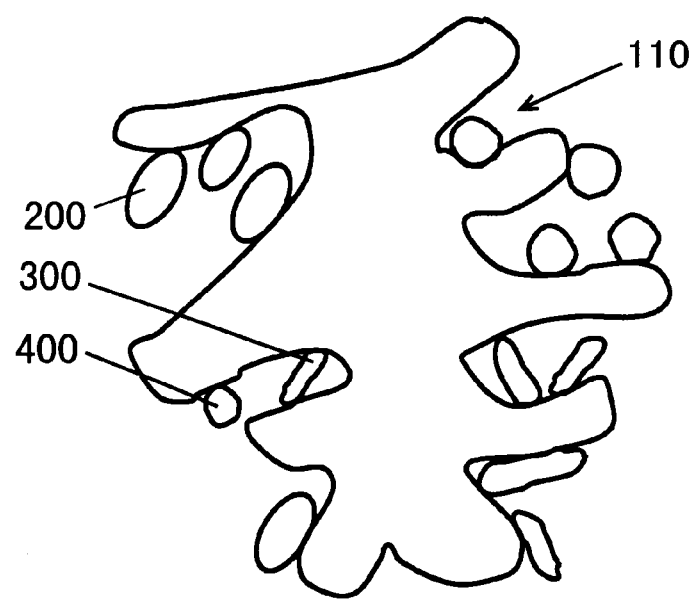
FIG. 2 shows the carrier for extracting bacteria shown in FIG. 1 in a state contained in a tank.

FIG. 2 is a model sectional view showing the bacteria extractive carrier 100 in the tank.

As shown in FIG. 2, a number of bacteria 200, 300 and 400 enter the plurality of pores 110 of the bacteria extractive carrier 100. Thus, the bacteria 200, 300 and 400 inhabit in the bacteria extractive carrier 100 in a concentrated state. Particularly when setting the water retention and the temperature of the bacteria extractive carrier 100 in states excellent for inhabitation of the bacteria while impregnating the bacteria extractive carrier 100 with nutrients preferred by the bacteria 200, 300 and 400, the bacteria 200, 300 and 400 inhabit in the bacteria extractive carrier 100 in a highly concentrated state.

After a lapse of the prescribed period from starting driving the garbage disposal, the bacteria extractive carrier 100 is recovered from the tank and washed with a sterilized 0.85% salt solution. In this case, the bacteria 200, 300 and 400 entering the pores 110 are hardly removed from the bacteria extractive carrier 100. On the other hand, foreign matter such as the wood chips and kitchen garbage and microorganisms larger than the pore diameter remaining outside the pores 110 can be readily removed by washing.

Then, the washed bacteria extractive carrier 100 is crushed to detach the bacteria 200, 300 and 400 therefrom. The bacteria 200, 300 and 400 are detached by ultrasonic treatment if necessary. Further, the bacteria 200, 300 and 400 are separated from the bacteria extractive carrier 100 by sedimenting or centrifugation. Thus, the bacteria 200, 300 and 400 are extracted from the tank.

In the aforementioned method of extracting bacteria, the bacteria 200, 300 and 400 can be collected from the tank in a concentrated state by employing the bacteria extractive carrier 100 having the plurality of pores 110.

Further, foreign matter larger than the pore diameter can be readily removed by washing, to require no operation such as filtration for removing the foreign matter. In addition, the bacteria extractive carrier 100 is made of a material having no DNA, whereby DNA of the bacteria 200, 300 and 400 can be analyzed with no hindrance even if the extracted bacteria 200, 300 and 400 contain the bacteria extractive carrier 100.

In the method of extracting bacteria according to this embodiment, as hereinabove described, bacteria can be readily extracted from the tank of a garbage disposal.

The inventive method of extracting a microorganism is not restricted to extraction of bacteria but is also applicable to extraction of microorganisms such as protozoa. In this case, the pores of the carrier are set in response to the size of the microorganisms to be extracted.

A method of assaying bacteria extracted by the above method of extracting bacteria is now described.

In the following description, bacteria extracted from the tank of a garbage disposal by the above method of extracting bacteria are assayed.

Figure 3:
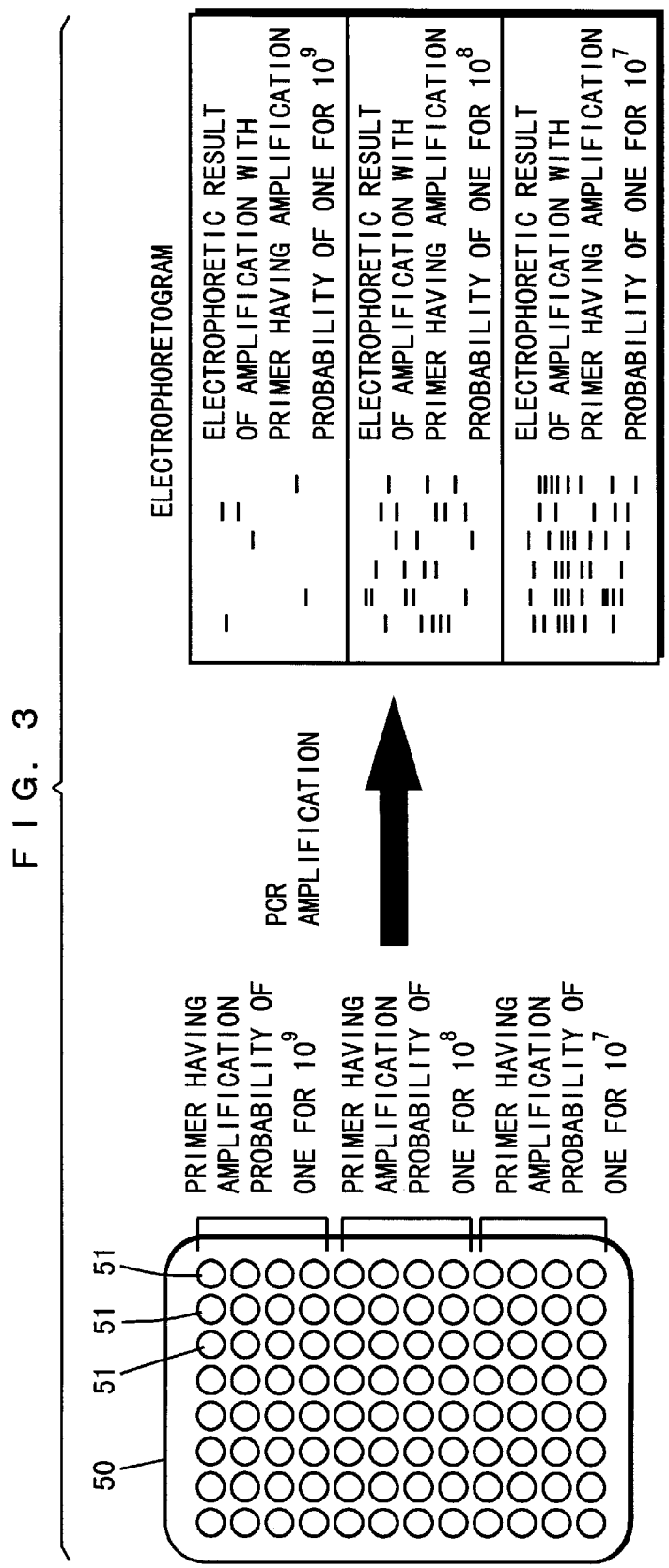
FIG. 3 is a model diagram showing an exemplary apparatus for amplifying DNA fragments employed for a method of assaying microorganisms according to the embodiment of the present invention.

FIG. 3 is a model diagram showing an exemplary apparatus for amplifying DNA fragments employed for the method of assaying bacteria.

Referring to FIG. 3, the apparatus for amplifying DNA fragments is formed by a support plate 50 called a titer plate. A plurality of openings (reaction solution storage parts) 51 are formed on the upper surface of the support plate 50. In the example shown in FIG. 3, 96 openings 51 are formed on the upper surface of the support plate 50.

Primers having an amplification probability for amplifying a DNA fragment for $10^8$ bp (base pairs) are arranged in 32 openings 51 closer to an end of the support plate 50. primers having an amplification probability for amplifying a DNA fragment for $10^8$ bp are arranged in 32 openings 51 at the center of the support plate 50. Primers having an amplification probability for amplifying a DNA fragment for $10^7$ bp are arranged in 32 openings 51 closer to another end of the support plate 50.

Figure 4:
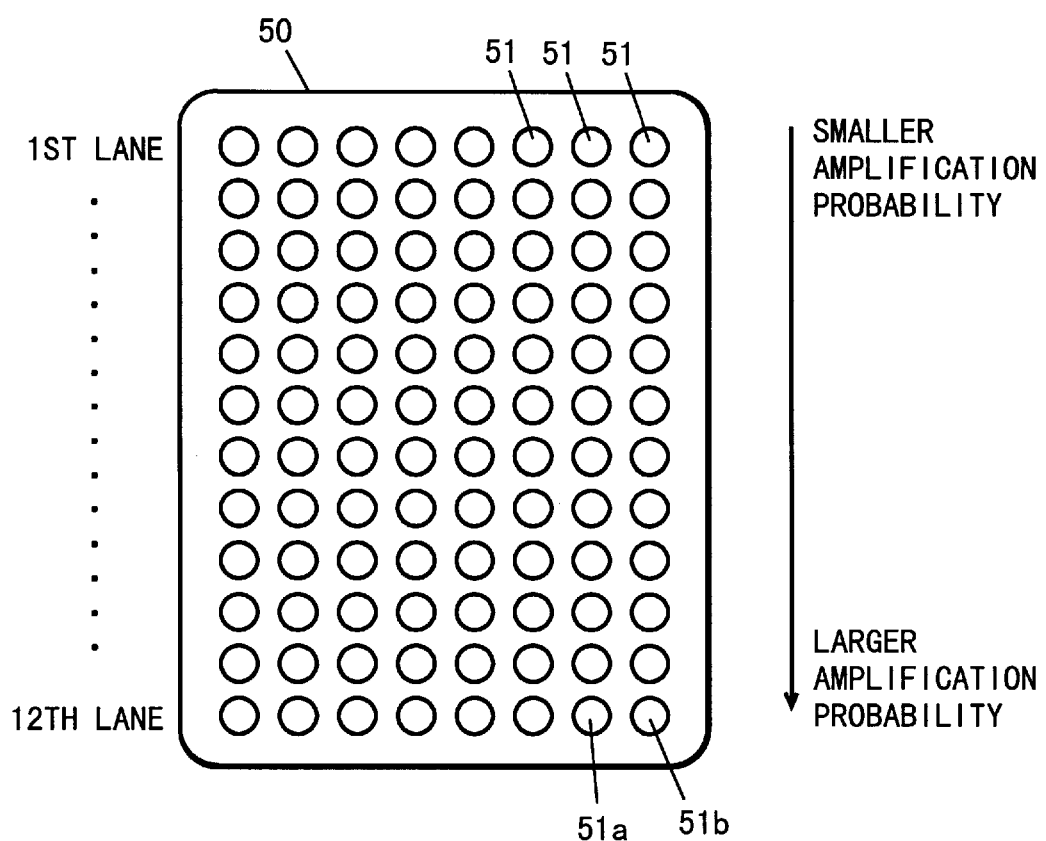
FIG. 4 is a model diagram showing another exemplary apparatus for amplifying DNA fragments employed for the method of assaying microorganisms according to the embodiment of the present invention.

FIG. 4 is a model diagram showing another exemplary apparatus for amplifying DNA fragments employed for the method of assaying bacteria according to this embodiment.

Also in the apparatus for amplifying DNA fragments shown in FIG. 4, a plurality of openings 51 are formed on the upper surface of a support plate 50. A plurality of primers having different amplification probabilities are continuously arranged in the plurality of openings 51 in order of the amplification probabilities.

Consider that the base length of chromosome DNA of bacteria is about $10^7$ bp. When setting the amplification probability to amplify a DNA fragment for $10^8$ bp in order to assay a bacteria flora containing 10 types of microorganisms, for example, a DNA fragment is amplified, i.e., a single type of bacterium is detected for 10 types of microorganisms. Therefore, 10 types of bacteria can be detected by preparing 10 types of primers. In practice, however, 20 to 30 types of primers are preferably prepared in order to cope with unbalanced amplification.

If the bacteria flora contains a number of bacteria or chromosome DNA of the bacteria has a large base length, it is effective to set the amplification probability at a low value. If the bacteria flora contains a small number of bacteria or the chromosome DNA of the bacteria has a small base length on the contrary, it is effective to set the amplification probability at a high value.

In the apparatus for amplifying DNA fragments shown in FIG. 3. primers having different amplification probabilities or different orders of amplification probabilities are arranged in order, while 32 types of primers are prepared for each amplification probability. In the apparatus for amplifying DNA fragments shown in FIG. 4, on the other hand, 96 types of primers having different amplification probabilities are prepared in order of the amplification probabilities.

A plurality of bacteria contained in the bacteria flora are simultaneously amplified with all primers by a random PCR (polymerase chain reaction) method described later. The random PCR method is a reaction method of chain-reactionally amplifying DNA fragments from a plurality of different microorganisms having unknown base sequences with primers having a specific base sequence.

As shown in FIG. 3, a number of bands appear in an electrophoretic pattern of DNA fragments amplified with primers having a high amplification probability. On the contrary, a small number of bands appear in an electrophoretic pattern of DNA fragments amplified with primers having a low amplification probability. Thus, bacteria can be analyzed on the basis of an electrophoretic pattern amplified at the optimum amplification probability in response to the number of types of bacteria contained in the object bacteria flora, the size of chromosomes of the bacteria, the number of types of DNA fragments or the size of the DNA fragments.

The random PCR method employed for the method of assaying bacteria according to this embodiment is now described.

In the random PCR method, the following three stages of steps are repeated similarly to the conventional PCR method. In this random PCR method, primers having a specific base sequence are employed for a plurality of different microorganisms having unknown base sequences thereby amplifying an analyzable quantity of DNA fragments, as described later.

(1) Thermal Denaturation Step

DNA (initial state) or a DNA fragment is heated and denatured into single strands (DNA strands).

(2) Primer Annealing Step (Primer Bonding Step)

Heat treatment is performed to bond a primer to an end of an amplification region of each DNA strand.

(3) Extension Reaction Step with Polymerase (Duplication Step with Polymerase)

Starting from the primer, a complementary strand is synthesized by polymerase to form a double strand.

A cycle formed by the aforementioned steps (1) to (3) is repeated.

The random PCR method is now described more specifically. First prepared is a reaction solution containing chromosome DNA of a plurality of different bacteria, a buffer solution for polymerase chain reaction, primers, heat-resistant thermophile DNA polymerase and four types of deoxyribonucleotide triphosphates (DATP, dGTP, dCTP and dTTP) serving as substrates.

The DNA polymerase is an enzyme having substrates of four types of 5'-deoxyribonucleotide triphosphates for catalyzing polymerization reaction of DNA strands having a base sequence complementary to template DNA. The directionality of polymerization of DNA strands with the DNA polymerase is at the 5' to 3' ends. The primers are DNA fragments (short oligonucleotldes) having 3'-OH groups essential for the action of the DNA polymerase on ends thereof. In this case, primers having a specific base sequence and a specific base length are employed.

The following random PCR method is applied to the aforementioned reaction solution:

As a first cycle, a thermal denaturation step of keeping the aforementioned reaction solution at 94° C. for two minutes, for example, a primer annealing step of keeping the aforementioned reaction solution at 45° C. for two minutes, for example, and an extension reaction step with polymerase for keeping the aforementioned reaction solution at 72° C. for three minutes, for example, are carried out in this order. The time for the thermal denaturation step in this cycle is set longer than those in second and third cycles, in order to completely separate long complete DNA into single strands.

Then, as the second cycle, a thermal denaturation step of keeping the aforementioned reaction solution at 94° C. for one minute, for example, a primer annealing step of keeping the aforementioned reaction solution at 45° C. for two minutes, for example, and an extension reaction step with polymerase for keeping the aforementioned reaction solution at 72° C. for three minutes, for example, are repeated in this order 33 times, for example.

Finally, as the third cycle, a thermal denaturation step of keeping the aforementioned reaction solution at 94° C. for one minute, for example, a primer annealing step of keeping the aforementioned reaction solution at 45° C. for two minutes, for example, and an extension reaction step with polymerase for keeping the aforementioned reaction solution at 72° C. for ten minutes, for example, are carried out in this order. In this cycle, the time for the extension reaction step with polymerase is set longer than those in the first and second cycles, in order to finally complete duplication.

Figure 5:
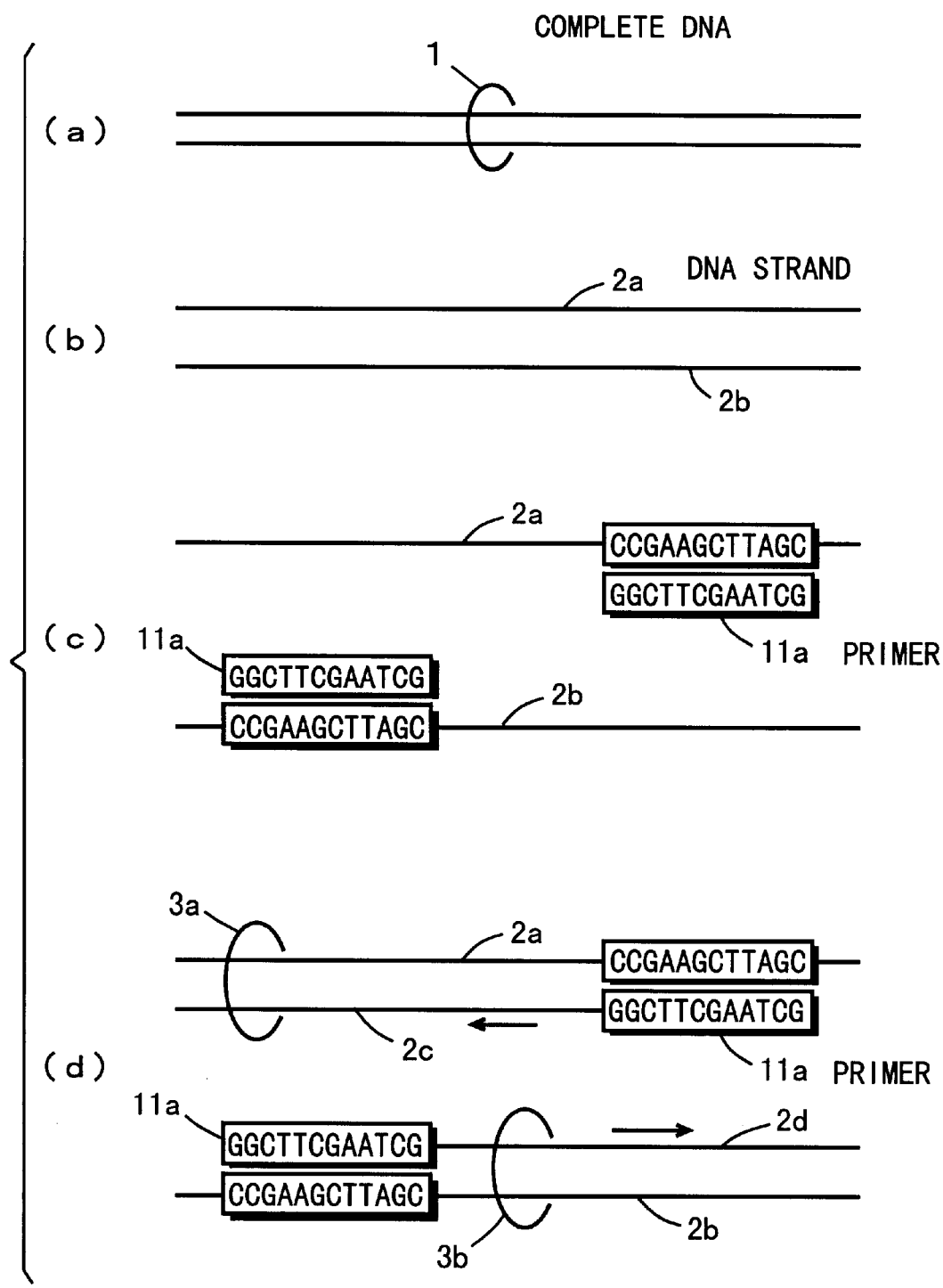
FIG. 5 is a model diagram showing the process in a first cycle in a random PCR method (GGCTTCGAATCG is SEW ID NO: 1 and CCGAAGCTTAGC is SEQ ID NO: 2)

The first cycle, a first time of the second cycle and a second time of the second cycle are now described with reference to FIGS. 5 to 7. FIGS. 5 to 7 are model diagrams showing single strands of DNA with the base sequence of parts bonded to the primers.

Referring to FIGS. 5 to 7, the primers have a base sequence (SEQ ID NO:1) of GGCTTCGAATCG. T stands for thymine, A for adenine, G for guanine, and C for cytosine.

As shown at (a) in FIG. 5, long DNA (complete DNA) 1 contained in a plurality of different bacteria initially exists in the aforementioned reaction solution. The following description is made with reference to single complete DNA 1.

First, the thermal denaturation step longer than those in the second and third cycles is carried out in the first cycle, so that the long DNA 1 is heated, denatured and separated from a double stranded state into two single strands (DNA strands) $2a$ and $2b$, as shown at (b) in FIG. 5.

Then, in the primer annealing step, each primer $11a$ is bonded to be arranged (complementarily arranged) on a compatible position of each of the single strands $2a$ and $2b$ compatible with its base sequence, as shown at (c) in FIG. 5. The term compatible position stands for the position of a base sequence (e.g., CCGAAGCTTAGC is {SEQ ID NO: 2} to be bonded as viewed from that of the primer or the position of a base sequence similar to that to be bonded as viewed from the base sequence of the primer. In the aforementioned random PCR method, the annealing temperature for the primer annealing step is set at a low level so that the primer is bonded also to a part of a DNA strand having a base sequence similar to its base sequence. In other words, the primer can be bonded not only to the position of a single strand having a base sequence completely complementary to its base sequence but also to the single strand with slight mismatching. Referring to FIGS. 5 to 7, each primer is bonded to the position of the base sequence to be bonded as viewed from its base sequence, for simplifying the illustration.

Then, in the extension reaction step with polymerase, extension reaction is caused by the polymerase so that single strands $2c$ and $2d$ extend along the single strands $2a$ and $2b$ respectively to form double strands $3a$ and $3b$, as shown at (d) in FIG. 5.

In the first time of the second cycle, the strands $3a$ and $3b$ doubled in the first cycle are separated into the single strands (DNA strands) $2a$ and $2c$ and the single strands (DNA strands) $2b$ and $2d$ respectively through the thermal denaturation step, while the following description is made with reference to the single strand $2c$ separated from the strand $3a$.

As shown in FIG. 6, a primer $11b$ is bonded to the single strand $2c$ separated through the thermal denaturation step to be arranged on a compatible position in the subsequent primer annealing step. Thereafter in the extension reaction step with polymerase, extension reaction is caused by the polymerase so that a single strand $2e$ extends along the single strand $2c$ to form a double strand $3d$.

Thereafter the double strand $3d$ is separated into the single strands $2c$ and $2e$ through the thermal denaturation step in the second time of the second cycle, while the following description is made with reference to the single strand $2e$ separated from the strand $3d$.

As shown in FIG. 7, a primer $11c$ is bonded to the single strand $2e$ separated through the thermal denaturation step to be arranged on a compatible position in the subsequent primer annealing step. Thereafter in the extension reaction step with polymerase, extension reaction is caused by the polymerase so that a single strand $2f$ extends along the single strand $2e$ to form a double strand (DNA fragment) $3e$.

The DNA fragment is thus formed so that another DNA fragment is formed from this DNA fragments while DNA fragments are formed from another DNA of the same type followed by chain-reactional continuation of similar reaction, whereby DNA fragments are amplified by this method.

Gel electrophoresis is applied to the DNA fragments amplified by the aforementioned random PCR method, in order to classify the same in response to different bacteria. The existential states of the bacteria can be estimated by analyzing bands on electrophoretic patterns. Alternatively, the aforementioned random PCR method is applied to bacteria sampled at time intervals for amplifying DNA fragments and gel electrophoresis is similarly applied to the amplified DNA fragments. Time change of the existential states of the bacteria can be estimated by analyzing state change of bands on electrophoretic patterns.

When applying the aforementioned random PCR method to a plurality of bacteria sampled from the tank of a garbage disposal or soil, the existential states of the bacteria in the tank of the garbage disposal or the soil can be estimated. When examining existential states of bacteria similarly sampled from the tank of the garbage disposal or the soil at time intervals, time change of the existential states of the bacteria in the tank of the garbage disposal or the soil can be estimated. In a degradation process of organic matter contained in kitchen garbage, further, the degradation state of the organic matter can also be estimated.

When changing the conditions of the tank of the garbage disposal in accordance with the results of estimation, kitchen garbage can be excellently treated while preparing excellent compost.

While the bacteria are extracted from the tank of the garbage disposal with the bacteria extractive carrier 100 according to the present invention so that the extracted bacteria are analyzed by the method of assaying bacteria in the above description, the present invention is also applicable to other cases. For example, the bacteria extractive carrier according to the present invention may be buried in soil for extracting bacteria from the soil and analyzing the same by the method of assaying bacteria. In this case, information of the bacteria in the soil can be obtained.

When the bacteria extractive carrier 100 is impregnated with a hardly degradable material such as an organochlorine compound (dioxin, PCB, dichloromethane, carbon tetrachloride, 1,2-dichloroethane, 1,1-dichloroethylene, cis-1,2-dichloroethylene, 1,1,1-trichloroethane, 1,1,2-trichloroethane, trichloroethylene, tetrachloroethylene or the like), an organic compound (benzene, toluene, xylene, phenol, benzoic acid or the like and a derivative thereof), cyanide, pesticide (1,3-dichloropropene, thiuram (tetramethylthiuram disulfide), simazine (2-chloro-4,6-bis (ethylamino)-s-triazine), thiobencarb (S-4-chlorobenzyl:N, N-diethyl thiocarbamato) or the like), an organophosphorus compound (parathion (diethyl-paranitrophenyl-thiophosphate), parathion-methyl (dimethilparanitrophenylthiophosphate), demeton-methyl (dimethylethylmercaptoethylthiophosphate), EPN (ethylparanitrophenylthionobenzenephosphonate) or the like), an ammonia-nitrogen compound, a nitrate-nitrogen compound or plastic (polyethylene, polystyrene, polypropylene, vinyl chloride resin, polyethylene terephthalate, urea resin, phenolic resin or the like), for example, or made of such a hardly degradable material and buried in soil, bacteria capable of degrading the hardly degradable material gather and inhabit in the bacteria extractive carrier 100. Thus, the bacteria capable of degrading the hardly degradable material can be detected from the soil by extracting and analyzing the bacteria inhabiting in the bacteria extractive carrier 100.

When the bacteria extractive carrier 100 is made of biodegradable plastic such as polycaprolactone, polybutylene succinate, polylactic acid, poly-3-hydroxybutyric acid, a copolymer of poly-3-hydroxybutyric acid and polyhydroxyvaleric acid, starch, a blend of polycaprolactone and starch, a copolymer of aliphatic polyester and polyamide, a copolymer of aliphatic polyester and aromatic polyester, ester polyurethane, a polymer containing sugar, cellulose, a mixture of chitosan and cellulose, poly-γ-methylglutamate or the like, for example, and buried in soil, bacteria capable of degrading the biodegradable plastic gather and inhabit in the bacteria extractive carrier 100. Thus, the bacteria capable of degrading the biodegradable plastic can be found from the soil by extracting the bacteria inhabiting in the bacteria extractive carrier 100. In this case, the bacteria extractive carrier 100 prepared from the biodegradable plastic itself is degraded by the bacteria, whereby the speed of degradation of the biodegradable plastic by the bacteria and the degradation state can be examined by measuring the weight, the degree of polymerization etc. of the bacteria extractive carrier 100 for examining optimum conditions for degradation.

Alternatively, a bacterium isolated from the group of bacteria is identified by biochemical examination while analyzing a band pattern of DNA of the identified bacterium by the aforementioned method of assaying microorganisms. Thus, the types of a plurality of bacteria and band patterns of DNA thereof may be analyzed for establishing a database of the band patterns of the DNA of the bacteria on the basis of the obtained data. In this case, DNA of a plurality of bacteria included in the group of bacteria sampled from soil in the aforementioned manner is analyzed by the aforementioned method of assaying bacteria and the types of the bacteria are retrieved from the database on the basis of the obtained band patterns of the DNA of the bacteria. Thus, the types of the bacteria forming the group of bacteria can be examined.

In particular, the aforementioned method of retrieving the types of the bacteria from the database is effective to find out soil, food or the like contaminated by toxic contaminants such as mercury, arsenic, dioxin, environmental hormones and the like. The database is searched on the basis of the band patterns of the DNA of the bacteria in the soil analyzed in the aforementioned manner for identifying the types of the bacteria forming the bacteria. When the identified bacteria include that related to any contaminant, such a possibility is suggested that the soil from which the bacteria have been sampled contains the contaminant. Further, the existential degree of the bacterium related to the contaminant suggests the contamination state of the soil. Tables 1 and 2 show exemplary contaminants and bacteria related thereto.

TABLE 1

| Classification | Substance Name | Related Microorganism |
| --- | --- | --- |
| Agricultural chemicals | organic phosphorus such as parathion | Pseudomonas diminuta |
| | carbamate | Achromobacter sp. |
| | triazine | Rhodocoocus sp. |
| | | Rhodococcus corallinus. |
| | | Phanerochaete chrysosporium |
| | organic chlorine | Alcaligenes eutrophus |
| | | Flavobacterium sp. |
| | | Pseudomonas cepacia |
| Insecticide | γ-BHC | Pseudomonas paucimobilis |
| | | Sphingomonas paucimobilis |
| | PCP | Rhodococous chlorophenolicus |
| | | Pseudomonas sp. |
| | | Phanerochaete chrysosporium |
| | | Phanerochaete sordida |
| Plastic | polyvinyl alcohol | Pseudomonas putida |
| | | Pseudomonas vesicuaris |
| | polyether (polyethylene glycol) | Pseudomonas aeruginosa |
| | | Bacteroides sp. |
| | | Pelolobacter venetianus |
| | | Rhizobium loti |
| | | Corynebacterium sp. |
| | | Sphingomonas pegritica |
| | polyester | Penicillium sp. |
| | polyurethane | Rhizobium delemar |
| | polyamide | Corynebacterium aurantiacum |
| | | Flavobacterium sp. |

TABLE 2

| Classification | Substance Name | Related Microorganism |
| --- | --- | --- |
| Metal | mercury | Pseudomonas sp. |
| | | Methanobacterium omelianskii |
| | | Clostridium cochlearium |
| | chromium | Streptococcus lactis |
| | | Alcaligenes eutrophus |
| | | Pseudomonas aeruginosa |
| | | Enterobacter cloacae |
| | cadmium | Staphlococcus aureus |
| | | Alcaligenes eutrophus |
| | aluminum | Chaetosphaeria inaegualis |
| | | Paecilomyces lilacinus |
| | | Metarhizium anisopliae |
| | | Penicillium glabrum |
| | | Aspergillus fumigatus |
| | | Sporothrix inflata |
| | | Emericellopsis minima |
| | iron | Thiobacillus ferrooxidans |
| | | Thiobacillus thiooxidans |

TABLE 2-continued

| Classification | Substance Name | Related Microorganism |
|---|---|---|
| | arsenic | *Leptospirillum ferooxidans*<br>*Alcaligenes faecalis*<br>*Pseudomonas* sp.<br>*Micrococcus lactilyticus*<br>*Staphylococcus aureus* |
| Chlorine<br>Organic<br>Compound | chlorobenzoic<br>acid | *Pseudomonas putida*<br>*Alcaligenes eutrophus* |

SEQUENCE LISTING

<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence:Primer
      sequence

<400> SEQUENCE: 1
ggcttcgaat cg                                                          12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence:Complement
      of Primer Sequence

<400> SEQUENCE: 2
ccgaagctta gc                                                          12

TABLE 2-continued

| Classification | Substance Name | Related Microorganism |
|---|---|---|
| | chlorobenzene<br>etc. | *Alcaligenes eutrophus* |
| | dioxin | *Phanerochaete chrysosporium* |

If the soil contains Methanobacterium, Clostridium or Pseudomonas as shown in Tables 1 and 2, for example, the possibility of soil contamination with mercury is suggested. Further, it is also possible to estimate presence/absence of dioxin and the existential degree thereof from existence of Phanerochaete which can degrade dioxin.

In order to generally examine presence/absence of contaminants in soil, food or the like, and degrees thereof, it is necessary to make analysis by a method suitable for each type of the contaminants. Particularly when examining the contamination state of organic matter, it is necessary to predict the contaminants for analyzing the same since the analytic methods for the elements contained in the organic matter vary. In general, therefore, it has been difficult to simultaneously examine a plurality of contaminants, while a large quantity of analytic samples must have been collected.

According to the aforementioned method of retrieving bacteria from the database of band patterns of DNA, on the contrary, the types of contaminants and the degrees thereof can be quickly examined by collecting a small quantity of samples of soil or food allowing no prediction of the contaminants and a sample containing a plurality of types of contaminants.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of extracting a microorganism comprising steps of:
   introducing a carrier for extracting a microorganism at a site for sampling microorganisms, said carrier being formed by a material body which has a plurality of pores and which does not comprise DNA;
   recovering said carrier for extracting a microorganism after a lapse of a prescribed time; and
   liberating said microorganisms from said recovered carrier for extracting a microorganism.

2. The method of extracting a microorganism in accordance with claim 1, wherein
   said pores of said carrier for extracting a microorganism have a mean pore diameter and a depth suitable for the size of said microorganisms to be extracted.

3. The method of extracting a microorganism in accordance with claim 1, further comprising a step of:
   liberating said microorganisms by crushing said carrier for extracting a microorganism.

4. The method of extracting a microorganism in accordance with claim 1, further comprising a step of:
   detaching said microorganisms from said carrier for extracting a microorganism by ultrasonic treatment.

5. The method of extracting a microorganism in accordance with claim 1, further comprising steps of:

crushing said carrier for extracting a microorganism; and detaching said microorganism from said crushed carrier by ultrasonic treatment and sedimenting or centrifuging said crushed carrier and said microorganisms.

6. The method of extracting a microorganism in accordance with claim 1, further comprising a step of:

crushing said carrier for extracting a microorganism by ultrasonic treatment; and centrifuging said crushed carrier and said microorganisms.

7. The method of extracting a microorganism in accordance with claim 1, further comprising a step of:

impregnating said carrier for extracting a microorganism with a nutrient preferred by a microorganism.

8. The method of extracting a microorganism in accordance with claim 5, wherein said material body is that degradable by a microorganism.

9. The method of extracting a microorganism in accordance with claim 1, wherein said material body is made of degradation-resistant plastic.

10. The method of extracting a microorganism in accordance with claim 1, wherein said material body is made of biodegradable plastic.

11. A method of assaying microorganisms comprising steps of:

introducing a carrier at a site for sampling a group of microorganisms, the carrier being formed by a material body, wherein the body has a plurality of pores and does not comprise DNA;

extracting the group of microorganisms by crushing said carrier, whereby said group of microorganisms is liberated from said carrier;

amplifying DNA obtained from said group of microorganisms by polymerase chain reaction using a plurality of primers having different amplification probabilities, whereby amplified DNA fragments are obtained;

classifying said amplified DNA fragments by a discrimination method; and discriminating said plurality of different microorganisms included in said group of microorganisms.

12. The method of assaying microorganisms in accordance with claim 11, wherein said DNA is amplified using an apparatus having said plurality of primers individually arranged in a plurality of wells in said apparatus.

13. The method of assaying microorganisms in accordance with claim 11, wherein said discrimination method is electrophoresis.

14. The method of assaying microorganisms in accordance with claim 11, further comprising steps of:

amplifying DNA of a reference microorganism related to a contaminant by polymerase chain reaction using said plurality of primers, whereby an amplified reference DNA fragment is obtained;

classifying said reference DNA fragment by a discrimination method;

preserving the relation between the type of said reference microorganism and the result of classification in a database; and retrieving the types of said group of microorganisms from said database on the basis of the results of classification of said amplified DNA fragments.

15. The method of assaying microorganisms in accordance with claim 14, further comprising a step of:

determining presence/absence of said contaminant in a site for sampling said microorganisms on the basis of the result of retrieval of said database.

16. The method of assaying microorganisms in accordance with claim 14, further comprising a step of:

determining the degree of the quantity of said contaminant in a site for sampling said microorganisms on the basis of the result of retrieval of said database.

17. The method of assaying microorganisms in accordance with claim 14, wherein said database preserves a plurality of types of microorganisms and results of classification corresponding thereto.

* * * * *